(12) United States Patent
Maas et al.

(10) Patent No.: US 6,737,555 B1
(45) Date of Patent: May 18, 2004

(54) METHOD FOR OLIGOMERIZING $C_6$-OLEFINS

(75) Inventors: Heiko Maas, Schifferstadt (DE); Peter Schwab, Bad Dürkheim (DE); Ralf Schulz, Speyer (DE); Marc Walter, Frankenthal (DE); Wolfgang Brox, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/914,532

(22) PCT Filed: Feb. 25, 2000

(86) PCT No.: PCT/EP00/01578

§ 371 (c)(1),
(2), (4) Date: Aug. 30, 2001

(87) PCT Pub. No.: WO00/53546

PCT Pub. Date: Sep. 14, 2000

(30) Foreign Application Priority Data

Mar. 8, 1999 (DE) .......................................... 199 10 103

(51) Int. Cl.$^7$ .............................. C07C 2/08; C07C 2/10

(52) U.S. Cl. ...................... 585/531; 585/532; 585/533
(58) Field of Search .................................. 585/531, 532, 585/533

(56) References Cited

U.S. PATENT DOCUMENTS

| | | | |
|---|---|---|---|
| 4,959,491 A | 9/1990 | Threlkel | .......................... 56/74 |
| 5,243,118 A * | 9/1993 | Sanderson et al. | .......... 585/515 |
| 5,849,972 A | 12/1998 | Vicari et al. | ................ 585/531 |

FOREIGN PATENT DOCUMENTS

| | | |
|---|---|---|
| DE | 39 14817 | 11/1990 |
| DE | 43 39 713 | 5/1995 |
| EP | 395 857 | 11/1990 |

* cited by examiner

Primary Examiner—Thuan D. Dang
(74) Attorney, Agent, or Firm—Oblon, Spivak, McClelland, Maier & Neustadt, P.C.

(57) ABSTRACT

In a process for oligomerizing $C_6$-olefins by reactin of a $C_6$-olefin-containing reaction mixture over a nickel-containing fixed-bed catalyst, the reaction over the fixed-bed catalyst is run at a conversion to oligomerized $C_6$-olefins of not more than 30% by weight, based on the reaction mixture.

8 Claims, 1 Drawing Sheet

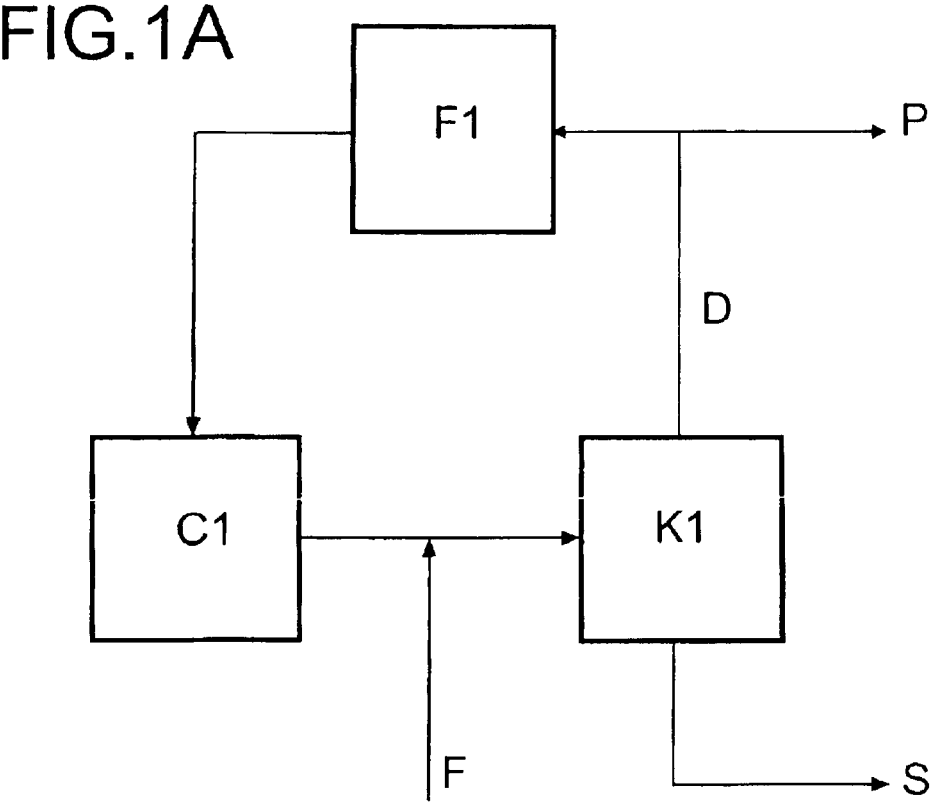
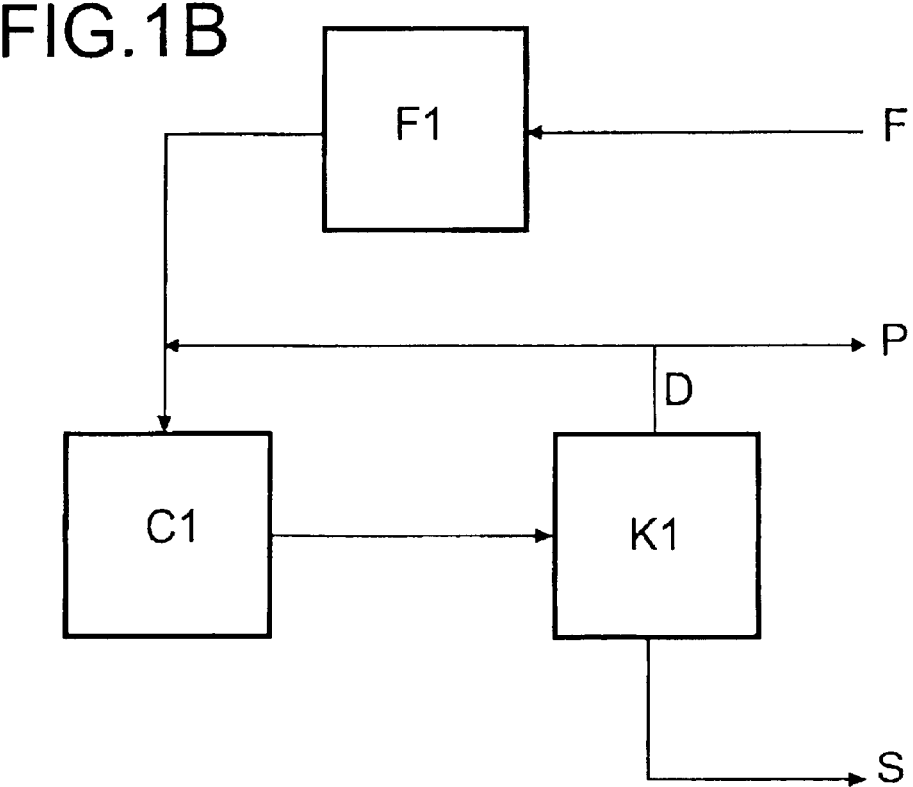

METHOD FOR OLIGOMERIZING $C_6$-OLEFINS

The present invention relates to a process for oligomerizing $C_6$-olefins, in particular for preparing $C_{12}$-olefins by dimerization.

Processes for the oligomerization of olefins are known. DE-A-43 39 713 describes a process for oligomerizing olefins to give highly linear oligomers. In this process, $C_{2-6}$-olefins are reacted at superatmospheric pressure and elevated temperature over a fixed-bed catalyst comprising from 10 to 70% by weight of nickel oxide, from 5 to 30% by weight of titanium dioxide and/or zirconium dioxide, from 0 to 20% by weight of aluminum oxide as significant active constituents and silicon dioxide as the remainder.

U.S. Pat. No. 4,959,491 describes a process for dimerizing $C_6$-olefins to form $C_{12}$-olefins which can be used for preparing surfactants. Catalyst used are nickel-containing catalysts such as hexafluoro-acetoacetylnickel (cyclooctadiene).

DE-A-39 14 817 describes a process for oligomerizing $C_{2-8}$-olefins, in which the reaction is carried out over nickel-exchanged montmorillonite, a nickel-aluminum-silicon oxide catalyst or nickel-impregnated molecular sieves or zeolites. The olefin mixture used is passed over a molecular sieve prior to the catalytic reaction.

A disadvantage of the known processes is that the catalyst life is frequently too short. The catalyst is, in particular, clogged by higher oligomers and therefore loses its activity.

It is an object of the present invention to provide a process for oligomerizing $C_6$-olefins which avoids the disadvantages of the known processes.

We have found that this object is achieved by a process for oligomerizing $C_6$-olefins by reaction of a $C_6$-olefin-containing reaction mixture over a nickel-containing fixed-bed catalyst, wherein the reaction over the fixed-bed catalyst is run at a conversion to oligomerized $C_6$-olefins of not more than 30% by weight, based on the reaction mixture.

The reaction over the fixed-bed catalyst is preferably carried out at a conversion of from 10 to 30% by weight, particularly preferably from 10 to 25% by weight, based on the reaction mixture. The oligomerization is preferably essentially a dimerization.

According to the present invention, it has been found that deactivation of the catalyst can be avoided and the dimer selectivity can be increased if the conversion over the catalyst is in the range indicated. The process can be carried out batchwise or continuously. It is preferably carried out continuously in the liquid phase. The conversion is then based on a throughput of the reaction mixture through the catalyst.

The reaction is preferably carried out at from 30 to 300° C. and a pressure in the range from 10 to 300 bar.

In order to achieve a high total conversion in the process, part of the unreacted reaction mixture obtained can, after separating off the oligomers, be returned to the reaction. Adjustment of the recycled amount of reaction mixture enables very high total conversions to be achieved. The term "oligomers" includes dimers and higher-boiling compounds.

The process of the present invention makes it possible to realize a total conversion of over 90% together with a $C_{12}$ selectivity of over 80%. Adherence to the conversion specified according to the present invention over the catalyst (based on a single pass) greatly increases the operating life of the catalyst, since the formation of high-boiling compounds which can deposit on the catalyst and thus cause a drop in activity is suppressed.

$C_6$-olefins which are suitable for use in the process of the present invention can be synthesized on an industrial scale by methods such as propylene dimerization. The most important industrial propylene dimerization processes are described, for example, in A. Chauvel and G. Lefebvre, Petrochemical Process, Edition Technip (1989), pp. 183 to 187 and F. Asinger, Die petrochemische Industrie, Akademier-Verlag (1971), pp. 278 to 299. The oligomerization is carried out industrially in the presence of either homogeneous or heterogeneous catalysts. The heterogeneous catalysts which can be used are listed in, for example, C.T. O'Connor et al., Catalysis Today Vol. 6 (1990), pp. 329 to 349.

The most important, based on the amount produced, homogeneously catalyzed process is the Dimnerol-G process of IFP. It is described in detail in Erdöl, Erdgas and Kohle, number 7/8, July/August 1990, pp. 309 to 315. The product obtained by means of this process (known as "Dimate") has the following average olefin

| | |
|---|---|
| $C_3$: | 4% by weight |
| $C_6$: | 73% by weight |
| $C_9$: | 17% by weight |
| $C_{12}$: | 4% by weight |
| $C_{15+}$: | 2% by weight |

The $C_6$ fraction is composed of:

| | |
|---|---|
| 4-methyl-1-pentene: | 0.9% by weight |
| 2,3-dimethyl-1-butene: | 2.3% by weight |
| cis-4-methyl-2-pentene: | 3.1% by weight |
| trans-4-methyl-2-pentene: | 21.7% by weight |
| 2-methyl-1-pentene: | 5.0% by weight |
| 1-hexene: | 0.3% by weight |
| trans-3-hexene: | 4.4% by weight |
| cis-3-hexene: | 0.7% by weight |
| trans-2-hexene: | 13.6% by weight |
| 2-methyl-2-pentene: | 39.2% by weight |
| cis-2-hexene: | 3.7% by weight |
| 2,3-dimethyl-2-butene: | 4.8% by weight |

Another source of $C_6$-olefins is provided by metathesis processes.

Possible catalysts are generally nickel-containing catalysts known per se which give little branching, as are described, for example, in Catalysis Today vol. 6 (1990), pp. 336 to 338, DE-A43 39 713, U.S. Pat. No. 5,169,824, DD2 73 055, DE-A-20 51 402, EP-A-0 202 670, Appl. Catal. 31 (1987), pages 259 –266, EP-A-0 261 730, NL 8 500 459, DE-A-23 47 235, U.S. Pat. No. 5,134,242, EP-A-0 329 305, U.S. Pat. Nos. 5,146,030, 5,073,658, 5,113,034 and 5,169,824.

In a preferred embodiment of the process of the present invention, the oligomerization is carried out in the liquid phase using the catalysts described in DE-A 43 39 713.

The catalysts described there consist essentially of nickel oxide, silicon oxide, titanium oxide and/or zirconium oxide and, if desired, aluminum oxide and have a nickel oxide content of from 10 to 70% by weight, a content of titanium dioxide and/or zirconium dioxide of from 5 to 30% by weight and an aluminum oxide content of from 0 to 20% by weight, with the remainder being silicon dioxide. They are obtainable by precipitation of the catalyst composition at a pH of from 5 to 9 by addition of an aqueous solution of nickel nitrate to an alkali metal water glass solution containing titanium oxide and/or zirconium dioxide, filtration, drying and heating at from 350 to 650° C.

The catalysts preferably contain essentially from 10 to 20% by weight of titanium dioxide, from 0 to 10% by weight of aluminum oxide and from 40 to 60% by weight of nickel oxide as main constituent and active component and silicon dioxide as the remainder.

Especially preferred catalysts have the composition 50% by weight of NiO, 34% by weight of $SiO_2$, 3% by weight of $Al_2O_3$ and 13% by weight of $TiO_2$. They are largely free of alkali metals ($Na_2O$ content <0.3% by weight).

The catalysts are preferably arranged in a fixed bed and are therefore preferably in the form of discrete bodies, e.g. in the form of pellets (5 mm ×5 mm, 5 mm ×3 mm, 3 mm ×3 mm), rings (7 mm ×7 mm ×3 mm, 5 mm ×5 mm ×2 mm, 5 mm ×2 mm ×2 mm) or extrudates (1.5 mm diameter, 3 mm diameter, 5 mm diameter).

In the process of the present invention, preference is given to reacting a hydrocarbon stream comprising n-hexene and/or methylpentene, preferably in the liquid phase, over the abovementioned Ni-containing catalysts.

Suitable $C_6$-hydrocarbons are, for example, mixtures having the following composition:

| paraffin: | from 10 to 90% by weight |
| olefin: | from 10 to 90% by weight, | where the olefin fraction can have the following composition:

| n-hexenes: | preferably from 0.1 to 99.8% by weight |
| methylpentenes: | preferably from 0.1 to 99.8% by weight |
| dimethylbutenes: | preferably from 0.1 to 99.8% by weight |

The hydrocarbon streams used are advantageously freed of oxygen-containing compounds such as alcohols, aldehydes, ketones or ethers by adsorption using a protective bed such as molecular sieves, aluminum oxides, aluminum oxide-containing solids, aluminum phosphates, silicon dioxides, kieselguhr, titanium dioxides, zirconium dioxides, phosphates, carbonontaining adsorbents, polymer adsorbents or mixtures thereof, as is known per se from DEA 39 14 817.

The oligomerization reaction takes place at from 30 to 300° C., preferably from 80 to 250° C. and in particular from 100 to 200° C., and a pressure of from 10 to 300 bar, preferably from 15 to 100 bar and in particular from 20 to 70 bar. The pressure is advantageously chosen so that the feed mixture is in liquid form at the temperature set. The reactor is generally a cylindrical reactor or shaft oven charged with the catalyst and the liquid reaction mixture flows through it from the top downward. After leaving the single-stage or multistage reaction zone, the oligomers formed are separated from the unreacted $C_6$-hydrocarbons in a manner known per se (e.g. by distillation) and all or most of the latter is returned to the reaction (however, a certain purge to remove inerts, e.g. hexane, is always necessary).

A useful aspect of the method of carrying out the reaction provided by the present invention is the opportunity of carrying out the process adiabatically in a shaft oven, since the heat generated in the reactor can be controlled as desired by dilution of the hexenes with the recirculated stream by choosing the amount and temperature of this stream. Compared to an isothermally operated process, the adiabatic procedure leads to a considerable reduction in the capital costs of the apparatus.

In one embodiment of the invention, it is possible to fractionate the feed mixture in a column (K) to separate $C_6$-olefins and oligomers ($C_{7+}$-hydrocarbons) prior to the reaction, to pass the $C_6$-olefins to the reaction (C1), to return the reacted mixture to the column (K1) and to discharge the oligomers ($C_{7+}$-hydrocarbons).

In a further embodiment, it is possible to fractionate the reacted mixture after the reaction in a column (K1) to separate $C_6$-olefins and oligomers, to return the $C_6$-olefins to the reaction (C1) and to discharge the oligomers.

The two abovementioned variants are shown schematically in FIG. 1a) and b) in the accompanying drawing.

In the figures, the symbols have the following meanings:

| F1: | protective bed |
| C1: | reactor |
| K1: | column |
| F: | feed |
| P: | purge |
| D: | distillate |
| S: | bottoms |

The protective bed (F1) serves to remove catalyst poisons (essentially S—N—O—containing hydrocarbons).

The fractionation of the oligomers is carried out in a manner known per se by fractional distillation to separate off the desired dodecenes. The sulfur-free $C_{13+}$ fraction displays a high blend value in respect of mixing into the diesel fuel pool. This $C_{13+}$ fraction is particularly preferably used as diesel fuel component after the olefins have been converted into paraffins by hydrogenation. This measure increases the cetane number which is a critical measure of the properties of the diesel fuel. All methods known from the prior art can be used for the hydrogenation.

The dodecenes obtained from the hexene dimerization can be further processed to produce surfactants.

The following examples illustrate the process of the present invention.

EXAMPLES

The experimental plant comprises the following plant items (process diagram as in FIG. 1):

adsorber for removing catalyst poisons (F1, volume: about 50 l)

adiabatic reactor (C1, volume: about 40 l, length: 8 m, diameter 80 mm)

distillation column (K1) for separating unreacted $C_6$-olefins and the oligomers formed [$C_{12}$].

The catalyst used was a material which had been produced in the form of 5 mm×5 mm pellets as described in DE-A 43 39 713. Composition in % by weight of the active components: 50% by weight of NiO, 13% by weight of $TiO_2$, 34% by weight of $SiO_2$, 3% by weight of $Al_2O_3$.

As adsorbent, use was made of a high surface area aluminum oxide such as Selexsorbo ® from Alcoa.

Example 1

The feed mixture used was a hydrocarbon mixture having the following composition:

| $C_3$: | 4% by weight |
| $C_6$: | 73% by weight |
| $C_9$: | 17% by weight |
| $C_{12}$: | 4% by weight |
| $C_{15+}$: | 2% by weight |

The $C_6$ fraction is composed of:

| | |
|---|---|
| 4-methyl-1-pentene: | 0.9% by weight |
| 2,3-dimethyl-1-butene: | 2.3% by weight |
| cis-4-methyl-2-pentene: | 3.1% by weight |
| trans-4-methyl-2-pentene: | 21.7% by weight |
| 2-methyl-1-pentene: | 5.0% by weight |
| 1-hexene: | 0.3% by weight |
| trans-3-hexene: | 4.4% by weight |
| cis-3-hexene: | 0.7% by weight |
| trans-2-hexene: | 13.6% by weight |
| 2-methyl-2-pentene: | 39.2% by weight |
| cis-2-hexene: | 3.7% by weight |
| 2,3-dimethyl-2-butene: | 4.8% by weight. |

The hydrocarbon mixture was introduced into the column K1 (FIG. 1A) at a rate of 5.1 kg/h. The following conditions were set in the experimental plant:

| | |
|---|---|
| Adsorption section: | |
| Pressure (bar) | 15 |
| Temperature (° C.) | 35 |
| Throughput (kg/h) | 18.8 |
| Synthesis section: | |
| Amount of catalyst (kg) | 25 |
| Pressure (bar) | 15 |
| Inlet temperature (° C.) | 100 |
| Outlet temperature (° C.) | 139 |
| Throughput (kg/h) | 18.8 |
| Distillation section: | |
| Pressure (bar) | 1 |
| Temperature - top (° C.) | 35 |
| Temperature - bottom (° C.) | 185 |
| Amount fed in (kg/h) | 23.9 |
| Distillate (kg/h) | 19.0 |
| Purge (kg/h) | 0.2 |
| Bottoms (kg/h) | 4.9 |

The following result was achieved:

| Stream | $C_3$ | $C_6$ | $C_9$ | $C_{12}$ | $C_{15+}$ | Total $C_{9+}$ |
|---|---|---|---|---|---|---|
| Feed mixture to K1 = reactor output | 1.7 | 78.1 | 3.7 | 13.4 | 3.1 | 20.2 |
| Distillate from K1 | 2.1 | 97.9 | <0.1 | <0.1 | <0.1 | — |
| Bottoms from K1 | <0.1 | 0.4 | 17.7 | 64.7 | 17.2 | 99.6 |

This gives a $C_6$-olefin conversion of 94.7% and a $C_{12}$ selectivity of 83.6% (based on the $C_6$-olefins reacted).

Example 2

The feed mixture used was a hydrocarbon mixture having the following composition:

| | |
|---|---|
| $C_5$: | 0.9% by weight |
| $C_6$: | 98.7% by weight |
| $C_7$: | 1.2% by weight |

The $C_6$ fraction is composed of:

| | |
|---|---|
| 4-methyl-1-pentene: | <0.1% by weight |
| 2,3-dimethyl-1-butene: | <0.1% by weight |
| cis-4-methyl-2-pentene: | <0.1% by weight |
| trans-4-methyl-2-pentene: | <0.1% by weight |
| 2-methyl-1-pentene: | <0.1% by weight |
| 1-hexene: | <0.1% by weight |
| trans-3-hexene: | 90% by weight |
| cis-3-hexene: | 10% by weight |
| trans-2-hexene: | <0.1% by weight |
| cis-2-hexene: | <0.1% by weight |
| 2-methyl-2-pentene: | <0.1% by weight |
| 2,3-dimethyl-2-butene: | <0.1% by weight. |

The hydrocarbon mixture was introduced into the filter F1 (FIG. 1B) at a rate of 3.20 kg/h. The following conditions were set in the experimental plant:

| | |
|---|---|
| Adsorption section: | |
| Pressure (bar) | 10 |
| Temperature (° C.) | 35 |
| Throughput (kg/h) | 3.20 |
| Synthesis section: | |
| Amount of catalyst (kg) | 25 |
| Pressure (bar) | 10 |
| Inlet temperature (° C.) | 100 |
| Outlet temperature (° C.) | 133 |
| Throughput (kg/h) | 15.75 |
| Distillation section: | |
| Pressure (bar) | 1 |
| Temperature - top (° C.) | 45 |
| Temperature - bottom (° C.) | 182 |
| Amount fed in (kg/h) | 15.75 |
| Distillate (kg/h) | 12.60 |
| Purge (kg/h) | 0.05 |
| Bottoms (kg/h) | 3.15 |

The following result was achieved:

| Stream | $C_5$ | $C_6$ | $C_{7-11}$ | $C_{12}$ | $C_{13+}$ | Total $C_{7+}$ |
|---|---|---|---|---|---|---|
| Feed mixture to K1 = reactor output | <0.1 | 80.6 | 0.4 | 15.7 | 3.3 | 19.4 |
| Distillate from K1 | 0.1 | 99.9 | <0.1 | <0.1 | <0.1 | — |
| Bottoms from K1 | <0.1 | 0.4 | 1.3 | 81.2 | 17.1 | 99.6 |

This gives a $C_6$-olefin conversion of 98.4% and a $C_{12}$ selectivity of 82.6% (based on the $C_6$-olefins reacted).

We claim:

1. A process for oligomerizing $C_6$-olefins by reaction of a $C_6$-olefin-containing reaction mixture over a nickel-containing fixed-bed catalyst, comprising from 10 to 70% by weight of nickel oxide, from 5 to 30% by weight of titanium dioxide and/or zirconium dioxide and from 0 to 20% by weight of aluminum oxide as significant active constituents and silicon dioxide as the remainder, wherein the reaction over the fixed-bed catalyst is carried out continuously in the liquid phase and run at a conversion to oligomerized $C_6$-olefins of from 10 to 30% by weight based on a throughput of a reaction mixture through the catalyst in a single pass.

2. A process as claimed in claim 1, wherein the reaction over the fixed-bed catalyst is run at a conversion to oligomerized $C_6$-olefins of from 10 to 25% by weight, based on the reaction mixture.

3. A process as claimed in claim 1, wherein the oligomerization is essentially a dimerization.

4. A process as claimed in claim 1 carried out at from 30 to 300° C. and a pressure in the range from 10 to 300 bar.

5. A process as claimed in claim 1 which is carried out adiabatically in a shaft oven and in which part of the reaction mixture is returned to the reaction.

6. A process as claimed in claim 1, wherein a feed mixture is fractionated in a column to separate $C_6$-olefins and oligomers prior to the reaction, the $C_6$-olefins are returned to the reaction, the reaction mixture is returned to the column and the oligomers ($C_6$-hydrocarbons) are discharged.

7. A process as claimed in claim 1, wherein the reaction mixture after the reaction is fractionated in a column to seperate $C_6$-olefins and oligomers, the $C_6$-olefins are returned to the reaction and the oligomers are discharged.

8. A process as claimed in claim 1, wherein the reaction mixture is passed over a protective bed wherein catalyst poisons are removed, prior to the reaction.

* * * * *